Figure 2:
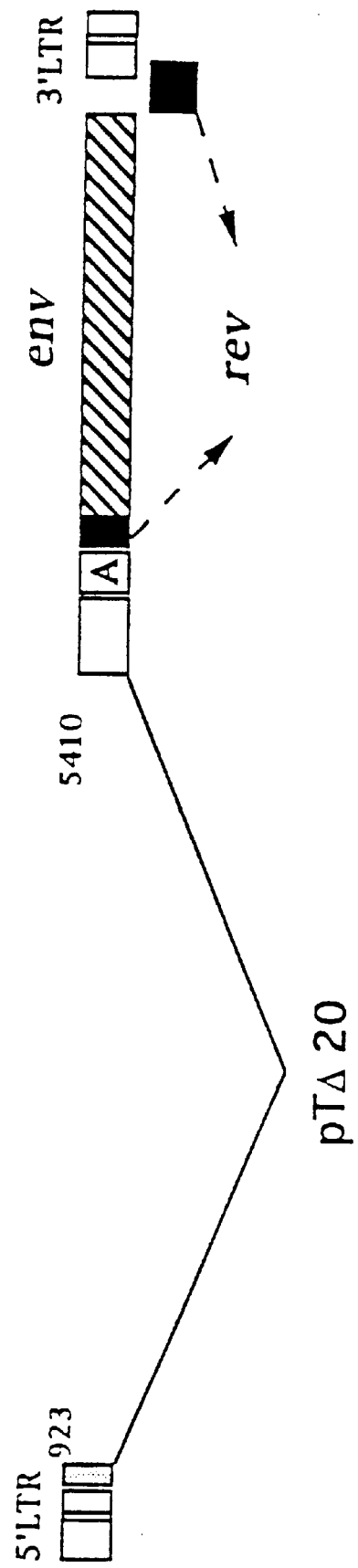

United States Patent [19]
Pancino et al.

[11] Patent Number: 5,994,516
[45] Date of Patent: Nov. 30, 1999

[54] MUTATED PROTEINS ENCODED BY A LENTIVIRUS MUTATED ENV GENE, PEPTIDE FRAGMENTS AND EXPRESSION VECTORS

[75] Inventors: Gianfranco Pancino; Pierre Sonigo, both of Paris, France

[73] Assignee: Centre National De La Recherche Scientifique-CNRS, Paris Cédex, France

[21] Appl. No.: 08/913,953
[22] PCT Filed: Mar. 26, 1996
[86] PCT No.: PCT/FR96/00449
§ 371 Date: Dec. 23, 1997
§ 102(e) Date: Dec. 23, 1997
[87] PCT Pub. No.: WO96/30527
PCT Pub. Date: Oct. 3, 1996

[30] Foreign Application Priority Data

Mar. 27, 1995 [FR] France ................................. 95 03566

[51] Int. Cl.[6] .......................... C07K 16/00; A61K 49/00; A61K 38/04; C12N 7/00
[52] U.S. Cl. .................................... 530/388.35; 424/9.34; 424/184.1; 424/188.1; 424/204.1; 424/208.1; 530/328; 530/350; 435/235.1; 536/23.72
[58] Field of Search ..................................... 530/328, 350, 530/388.35; 424/9.34, 184.1, 188.1, 204.1, 208.1; 435/235.1; 536/23.72

[56] References Cited

U.S. PATENT DOCUMENTS 5,648,209  7/1997  Avrameas et al. ......................... 435/5

OTHER PUBLICATIONS

Fox, J. L., No winners against AIDS, Bio/Technology, vol. 12, p. 128, see entire page, Feb. 1994.

Fahey et al., Status of immune–based therapies in HIV infection and AIDS, Clin. exp. Immunol. vol. 88, pp. 1–5, see page 3, second col., third full paragraph, Jan. 1992.

*Primary Examiner*—Jeffrey Stucker
*Assistant Examiner*—Hankyel T. Park
*Attorney, Agent, or Firm*—Oblon, Spivak, McClelland, Maier & Neustadt, P.C.

[57] ABSTRACT

Mutated proteins coded by a mutated env gene of a lentivirus, particularly FIV, HIV or CAEV, peptide fragments contained in said mutated proteins and expression vectors expressing said mutaded proteins as well as the applications thereof are described. The peptide fragments are contained in the principal immunodominant domain (PID) of the transmembrane protein (TM) of lentiviruses and particularly of feline immunodeficiency virus (FIV), human immounodeficiency virus (HIV-1 and HIV-2), arthritis virus and caprine encephalitis virus (CAEV), and are capable of modifying the immunogenic properties of the PID domain and of the Env protein of the lentiviruses containing them. Such fragments have one of the following sequences: SEQ ID No1: CNQNQWLCK, SEQ ID No2: CNQNQFLCK, SEQ ID No3: CNQNQLWCK, SEQ ID No4: CNQNQPFCK, SEQ ID No5: CEHQHFFCK, SEQ ID No6: CSMGTFFCK, SEQ ID No7: CLTDSFFCK, SEQ ID No8: CELKNFFCK, SEQ ID No9: CRFAAFFCK, SEQ ID No10: ELGCGSKLICKIP, SEQ ID No11: IWGCNQNQFFCTTAVPWN, SEQ ID No12: IWGVAFRQVCTTAVPW.

16 Claims, 3 Drawing Sheets

```
FIV       E L G C N Q N   Q F F C K I P         TM2 (FIV)  E L G C N Q N   Q F F C K I P
HIV-1LAI  I W G C S G K   L I C T T A           M1 (CAC)   E L G C - - -   - - - C K I P
HIV-1MAL  M V G C S G K   H I C T T F           M2 (S-S)   E L G S N Q N   Q F F S K I P
SIV-142   A W G C A F R   Q V C H T T           M3 (S-C)   E L G S N Q N   Q F F C K I P
HIV-2ROD  S W G C A F R   Q V C H T T           M4 (C-S)   E L G C N Q N   Q F F S K I P
CAEV      E L D C W H Y   H Q Y C V T S         M5 (HIV)   E L G C S G K   L I C K I P
VV        E L D C W H Y   Q H Y C V T S         M6 (VV)    E L G C W H Y   Q H Y C K I P
EIAV      L I G C I E R T H V F C H T G         M7 (EIAV)  E L G C I E R T H V F C K I P
                                                           1 2 3 4 5 6 7 8 9 10 11 12 13 14 15
              A                                                        B
```

```
FIV       E L G C N Q N     Q F F C K I P          TM2 (FIV)   E L G C N Q N   Q F F C K I P
HIV-1LAI  I W G C S G K     L I C T T A            M1 (CΔC)    E L G C - - -   - - - C K I P
HIV-1MAL  M V G C S G K     H I C T T F            M2 (S-S)    E L G S N Q N   Q F F S K I P
SIV-142   A W G C A F R     Q V C H T T            M3 (S-C)    E L G S N Q N   Q F F C K I P
HIV-2ROD  S W G C A F R     Q V C H T T            M4 (C-S)    E L G C N Q N   Q F F S K I P
CAEV      E L D C W H Y     H Q Y C V T S          M5 (HIV)    E L G C S G K     L I C K I P
VV        E L D C W H Y     Q H Y C V T S          M6 (VV)     E L G C W H Y   Q H Y C K I

MUTATED PROTEINS ENCODED BY A LENTIVIRUS MUTATED ENV GENE, PEPTIDE FRAGMENTS AND EXPRESSION VECTORS

This application is the national stage of PCT/FR96/00449, filed Mar. 26, 1996.

The present invention relates to mutated proteins encoded by a mutated env gene of a lentivirus, and in particular FIV, HIV or CAEV, to peptide fragments included in the said mutated proteins, to expression vectors expressing the said mutated proteins and to their applications.

Feline immunodeficiency is due to a lentivirus, the feline immunodeficiency virus (FIV), which has a genetic structure similar to that of the lentiviruses of primates (HIV and SIV).

A number of fragments have been selected and have allowed the development of sensitive and specific tests for the detection of seropositive animals, as described in European Patent Applications No. 0,564,477 of Nov. 20, 1991, No. 0,577,458 of Jun. 16, 1993, and French Patent Application No. 94 07062 of Jun. 9, 1994, in the name of the applicant, and are derived, for the majority, from the Env protein of FIV, comprising 854 amino acids, whose sequence is described in European Application 0,577,458, which provides, after cleavage, 2 glycoprotein fragments called SU (surface glycoprotein) and TM (transmembrane glycoprotein).

In particular, the TM protein includes several fragments of interest, namely:
a fragment including a segment of 51 amino acids, called TM1, which corresponds to positions 595–647 of the Env protein of FIV,
a fragment including a segment of 31 amino acids, called TM2, which corresponds to positions 681–711 of the Env protein of FIV, the said fragment contains an epitope including the sequence: $Cys^{697}$—Asn—Gln—Asn—Gln—Phe—Phe—Cys—$Lys^{705}$ (peptide called P237),
a fragment including a segment of 45 amino acids, called TM3, which corresponds to positions 744–788 of the Env protein of FIV, and
a fragment including a segment of 29 amino acids, called TM4, which corresponds to positions 826–854 of the Env protein of FIV.

Whereas in the field of detection, there are now available a range of reagents for the detection of FIV, in the field of immunoprotection, it has appeared that the principal immunodominant domain (PID) of the FIV envelope protein, comprising the abovementioned peptide P237, can cause the formation of antibodies which facilitate viral infection, whose action has a deleterious effect opposite that of the protective antibodies generated by vaccination with the Env protein (J. R. MASCOLA et al., AIDS Research & Human Retroviruses, 1993, 9, 12, 1175–1184).

In addition, a complete and mature envelope protein, in its oligomeric form, is preferable for inducing the formation of antibodies directed against conformation epitopes, among which are neutralizing antibodies (C. C. BRODER et al., Proc. Natl. Acad. Sci. USA, 1994, 91, 11699–11703).

It has appeared that the elimination and replacement of the Cys residues from the PID causes an envelope maturation defect which is no longer presented in its mature form at the surface of the infected cells (SYU W. J., 1991, J. Virol., 65, 6349–6352, DEDERA et al., J. Virol., 1992, 66, 1207–1209).

The two neighbouring cysteine residues of the peptide P237, conserved in the ectodomain of the TM, in most retroviruses, define a loop structure which is the major constituent of the PID. The amino acid sequence between the two cysteine residues is highly conserved in the same species of lentivirus, such as FIV or HIV. On the other hand, when the various species of lentivirus, for example HIV-1 and FIV, are compared, although the two cysteine residues are conserved, the amino acid sequences situated between these two residues do not exhibit any homology (FIG. 1A).

As regards HIV, the Principal Immunodominant Domain (PID) of the envelope of the human immunodeficiency type 1 virus (HIV-1) is highly conserved among the various viral isolates of HIV-1. The sequence between the two cysteines of the PID is also conserved among the HIV-1 subtypes, except for the 0 subtype (Outsider), which could correspond to a new type of HIV-1. The PID sequence of HIV-1 is completely different from that of HIV-2, which is, on the other hand, identical to that of the simian immunodeficiency virus (SIV), to which HIV-2 is phylogenetically related.

In general, the PID of lentiviruses can cause the formation of viral infection facilitating antibodies whose action has a deleterious effect opposite that of the protective antibodies generated by vaccination with the Env protein, as specified above, for the FIV envelope protein.

Consequently, the applicant set himself the objective of providing Env proteins mutated at the level of the said principal immunodominant domain (PID) of the transmembrane glycoprotein of lentiviruses and particularly of the feline immunodeficiency virus or of the human immunodeficiency virus, which exhibit a significantly different reactivity from that of the wild-type Env protein, particularly in that they do not induce the formation of deleterious, particularly facilitating, antibodies against the wild-type PID, while retaining the capacity to produce a protective immune response, including in particular neutralizing antibodies.

The subject of the present invention is, consequently, peptide fragments characterized in that they constitute mutants of the wild-type principal immunodominant domain (PID) of a wild-type transmembrane protein (TM) of lentiviruses and in particular of the feline immunodeficiency virus (FIV), the human immunodeficiency virus (HIV-1 and HIV-2) and the caprine arthritis and encephalitis virus (CAEV), which peptide fragments are capable of modifying the immunogenic properties of the PID, such that the Env protein of lentiviruses containing them does not cause the production of facilitating or deleterious antibodies against the wild-type PID, whereas it retains the capacity to produce neutralizing antibodies.

Mutant of the PID is understood to mean, for the purposes of the present invention, at least one sequence between the two cysteines of a wild-type PID of a TM protein of a lentivirus, which sequence is modified (1) either in that at least one amino acid is mutated, (2) or in that it comprises the sequence of a PID of a lentivirus Env protein different from that in which the said PID sequence is inserted. For practical reasons of insertion, the said peptide fragments may comprise downstream and/or upstream of the said sequence between the two cysteines, at least one additional amino acid.

Such peptide fragments therefore replace the principal immunodominant domain (PID) of a wild-type transmembrane protein (TM) of lentiviruses and in particular of the feline immunodeficiency virus (FIV), the human immunodeficiency virus (HIV-1 and HIV-2) and the caprine arthritis and encephalitis virus (CAEV) and constitute functional mutants of the PID of the Env protein into which they are inserted.

Among the said fragments, there may be mentioned:

the fragment CNQNQWLCK, called f8, (SEQ ID No. 1),
the fragment CNQNQFLCK, called fd, (SEQ ID No. 2),
the fragment CNQNQLWCK, called fh, (SEQ ID No. 3),
the fragment CNQNQPFCK, called fm, (SEQ ID No. 4),
the fragment CEHQHFFCK, called n14, (SEQ ID No. 5),
the fragment CSMGTFFCK, called n19, (SEQ ID No. 6),
the fragment CLTDSFFCK, called n67, (SEQ ID No. 7),
the fragment CELKNFFCK, called n73, (SEQ ID No. 8),
the fragment CRPAAFFCK, called n92, (SEQ ID No. 9),
the fragment ELGCSGKLICKIP, called M5, (SEQ ID No. 10),
the fragment IWGCNQNQFFCTTAVPWN (SEQ ID No. 11),
the fragment IWGVAFRQVCTTAVPW (SEQ ID No. 12).

The sequences ID No. 1 to ID No. 10 are functional mutants of the FIV PID; in particular, the sequence ID No. 10 contains the sequence of the HIV-1 PID in an FIV sequence (that is to say in the context of FIV), whereas SEQ ID Nos. 11 and 12 are functional mutants of the HIV-1 PID: SEQ ID No. 11 contains the sequence of the FIV PID in the context of HIV-1 (HIV-1/FIV chimera) and SEQ ID No. 12 contains the sequence of the SIV PID in the context of HIV-1 (HIV-1/SIV chimera). The sequences SEQ ID No. 1 to 9 are mutated sequences of the FIV PID.

The subject of the present invention is also Env proteins, characterized in that they are mutated at the level of the principal immunodominant domain (PID) of the transmembrane protein (TM) of lentiviruses and in particular of the feline immunodeficiency virus (FIV), the human immunodeficiency virus (HIV-1 and HIV-2) and the caprine arthritis and encephalitis virus (CAEV), and in that they comprise one of the fragments as defined above, at the level of the PID, which proteins do not cause the production of deleterious antibodies, in particular facilitating antibodies, against the wild-type PID, but conserve adequate conformation for the production of a protective immune response, including, in particular the production of neutralizing antibodies for a protective vaccine application.

The subject of the present invention is also vectors for expressing Env proteins of lentiviruses, characterized in that they comprise at least one mutated nucleic acid fragment encoding a mutated Env protein as defined above.

Surprisingly, such vectors allow the expression of a functional viral envelope, but whose immunological reactivity is significantly modified, in relation to that of the wild-type Env protein. Indeed, the mutated and expressed protein does not cause the production of facilitating antibodies against the wild-type PID, whereas it retains the capacity to produce neutralizing antibodies.

According to an advantageous embodiment of the said expression vector, it consists of an expression vector comprising a sequence encoding an Env protein of FIV, in which the sequence encoding PID (sequence 2077–2115, with reference to the sequence of formula I of application EP 0,577,458), is replaced by a sequence encoding any of the peptide fragments SEQ No. 1 to 10, as defined above.

The said vector may be advantageously constructed from a vector as described in G. PANCINO et al., Virology, 1995, 206, 796–806.

According to another advantageous embodiment of the said expression vector, it consists of an expression vector, comprising a sequence encoding a HIV-1 Env protein in which the sequence encoding the wild-type PID is replaced by a sequence encoding a mutant of the wild-type principal immunodominant domain (PID) of a wild-type transmembrane protein (TM), derived from the human immunodeficiency virus (HIV-1 and HIV-2) or of another lentivirus and capable of modifying the immunogenic properties of the PID; preferably, the said sequence encodes either of the peptide fragments SEQ No. 11 or 12, as defined above.

Preferably, the said sequences encoding PID are selected from the following sequences (SEQ ID No. 13 to 24):
sequence encoding the sequence ID No. 1: TGT AAT CAA AAT CAA TGG CTT TGC AAA (SEQ ID No. 13), for the production of the vector pf8Δ20,
sequence encoding the sequence ID No. 2: TGT AAT CAA AAT CAA TTT TTA TGC AAA (SEQ ID No. 14), for the production of the vector pfdΔ20,
sequence encoding the sequence ID No. 3: TGT AAT CAA AAT CAA TTG TGG TGC AAA (SEQ ID No. 15), for the production of the vector pfhΔ20,
sequence encoding the sequence ID No. 4: TGT AAT CAA AAT CAA CCT TTT TGC AAA (SEQ ID No. 16), for the production of the vector pfmΔ20,
sequence encoding the sequence ID No. 5: TGT GAA CAT CAG CAT TTT TTC TGC AAA (SEQ ID No. 17), for the production of the vector pn14Δ20,
sequence encoding the sequence ID No. 6: TGT AGT ATG GGG ACG TTT TTC TGC AAA (SEQ ID No. 18), for the production of the vector pn19Δ20,
sequence encoding the sequence ID No. 7: TGT TTG ACA GAT TCG TTT TTC TGC AAA (SEQ ID No. 19), for the production of the vector pn67Δ20,
sequence encoding the sequence ID No. 8: TGT GAA CTC AAA AAC TTT TTC TGC AAA (SEQ ID No. 20), for the production of the vector pn73Δ20,
sequence encoding the sequence ID No. 9: TGT CGG CCA GCT GCT TTT TTC TGC AAA (SEQ ID No. 21), for the production of the vector pn92Δ20,
sequence encoding the sequence ID No. 10: GAG CTC GGA TGT TCT GGA AAA CTC ATT TGC AAA ATC CCT (SEQ ID No. 22), for the production of the vector pM5Δ20,
sequence encoding the sequence ID No. 11: ATT TGG GGT TGC AAT CAA AAT CAA TTC TTC TGC ACC ACT GCA GTG CCT TGG AAT-3' (SEQ ID No. 23),
sequence encoding the sequence ID No. 12: ATT TGG GGT TGC GCG TTT AGA CAA GTC TGC ACC ACT GCA GTG CCT TGG AA-3' (SEQ ID No. 24).

The nucleic sequences according to the invention include all the sequences encoding the same amino acids (amino acid encoded by a codon different from that illustrated in sequences 13 to 24).

The subject of the present invention is also mutated lentivirus infectious molecular clones, characterized in that they include a sequence encoding a mutated Env protein, as defined above.

Preferably, the said mutated clones are obtained by introducing into an infectious molecular clone of FIV, preferably into the infectious molecular clone p34TF10, a fragment containing the abovementioned mutations at the level of the sequences encoding PID, in place of the corresponding wild-type sequences.

According to the mutated sequence introduced, the following clones are obtained: pTf8, pTfd, pTfh, pTn14, pTn19, pTn67, pTn73, pTn92 and pTM5.

Such clones are in particular obtained by incorporating into the genome of FIV p34TF10 SpeI-BstBI 8287–8918 fragments of the said genome of FIV p34TF10 containing the abovementioned mutations, in place of the corresponding wild-type sequences.

Also preferably, the said mutated clones are obtained by introducing into an infectious molecular clone of HIV-1 a fragment containing the abovementioned mutations at the level of the sequences encoding PID, in place of the corresponding wild-type sequences.

Such clones have the advantage of being able to be used directly as an attenuated live vaccine.

The subject of the present invention is also vaccine compositions, characterized in that they comprise at least one mutated Env protein and/or at least one expression vector and/or at least one mutated clone, as defined above.

The subject of the present invention is, in addition, a process for monitoring an anti-lentivirus vaccination and/or for differentiating between an anti-lentivirus vaccination and a lentivirus infection, characterized in that it comprises bringing a peptide fragment according to the invention into contact with a biological sample (blood in particular) and detecting the antigen (peptide fragment)-antibody (produced during the vaccination or during the infection) complex formed by any appropriate means.

In such a process, the mutated PID serves advantageously as marker sequence; indeed, the antibodies produced against the PID will be different in the case of vaccination (mutated PID) and in the case of infection (wild-type PID). In such a context, if a viral infection occurs during the vaccination, it will be effectively possible to distinguish it, the two immunological responses being different, because of the presence of the mutated PID and of the absence of the wild-type PID, in the vaccinal composition.

It is possible, for the wild-type PID, to use detection systems such as those described in European Patent Applications No. 0,564,477 of Nov. 20, 1991, No. 0,577,458 of Jun. 16, 1993, and French Patent Application No. 94 07062 of Jun. 9, 1994; to detect the mutated PIDs, it is possible to use similar detection systems, using the peptides of the mutated PID as defined above, as reagents, instead of the wild-type PID (see Example 1).

Figure 3:
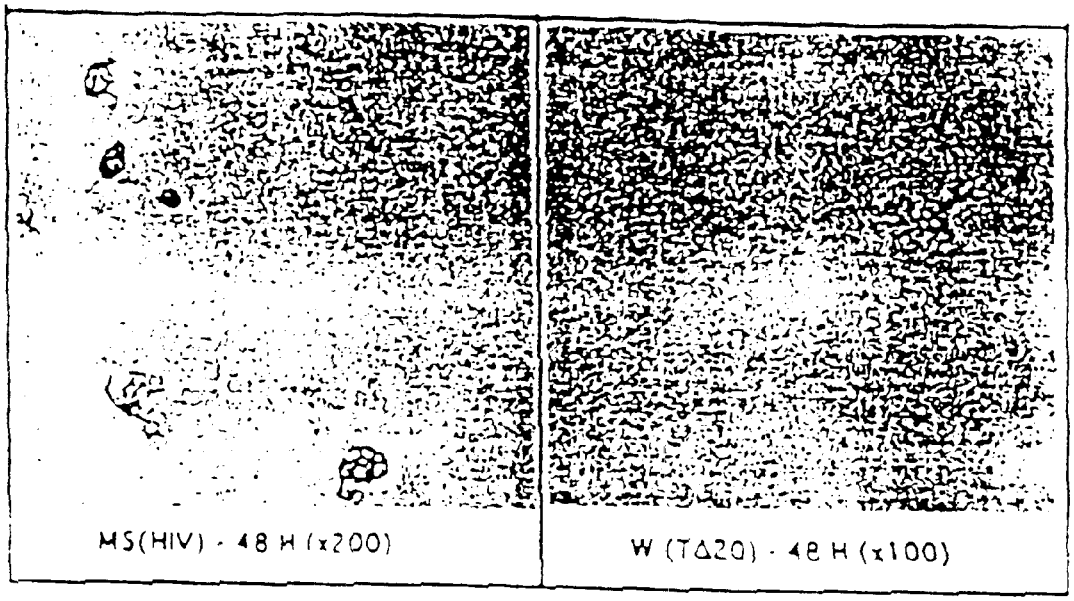

In addition to the above arrangements, the invention further comprises other arrangements which will emerge from the description which follows, which refers to exemplary embodiments of the process which is the subject of the present invention, as well as to the accompanying drawings, in which:

FIG. 1 represents the alignment of the sequences of the PIDs of the TM of various lentiviruses, FIG. 2 represents the vector for expression of the envelope pTΔ20, FIG. 3 represents the result of the fusion tests with the vector containing the M5 sequence.

It should be understood, however, that these examples are given solely by way of illustration of the subject of the invention and do not constitute in any manner a limitation thereto.

EXAMPLE 1

Construction of Mutants in the FIV Context
(Chimeras in which a PID of HIV Replaces the
Wild-Type PID of FIV, in an Env Sequence of
FIV)

The sequence encoding the Env protein of FIV is modified such that the sequences encoding the peptide fragments according to the invention as defined above (SEQ ID No. 1 to 10) are inserted, in place of the sequence encoding the abovementioned peptide P237 (positions 2077–2115 of the sequence encoding the Env protein as described in European Patent Application No. 0,577,458); the said sequences encoding an Env protein which are thus modified (mutant env sequences), are inserted into a vector called pTΔ20, which comprises a deletion from nucleotide 923 to nucleotide 5410 in the FIV gene (gag and pol genes).

The production of the vector pTΔ20 is described in G. PANCINO et al., Virology, 1995, 206, 796–806.

The Env expression vector pTΔ20 (FIG. 2) is derived from the infectious molecular clone of FIV p34TF10, by deletion of the gag and pol genes.

SpeI-BstBI 8287–8918 fragments of the env gene of FIV p34TF10, containing the abovementioned mutations are introduced into the expression vector, in place of the corresponding fragments containing the wild-type sequence.

To produce the env expression vector of FIV and to use it in feline cells, a deletion of the gag and pol genes is made in the provirus p34TF10 (TALBOTT et al., Proc. Natl. Acad. Sci. USA, 1989, 86, 5743–5747) by TthIII-EcoRV digestion and religation after treating with the Klenow enzyme.

A clone, called pTΔ20, which comprises a larger deletion, from nucleotide 923 to nucleotide 5410 effectively expresses the said Env protein, after transfection into the CrFK cells (Virology, 1995, 206, 796–806).

EXAMPLE 2

Mutated Peptides Obtained in Example 1 and Env
Proteins Containing Them: Functionality and
Reactivity Method:

To test the functionality of the mutated envelopes, the abovementioned expression vectors (pf8Δ20, pfdΔ20, pfhΔ20, pfmΔ20, pn14Δ20, pn19Δ20, pn67Δ20, pn73Δ20, pn92Δ20, pM5Δ20,) producing mutated Env proteins in accordance with the invention are transfected into CrFK cells and analyzed for their capacity to induce the fusion of the cell membranes (formation of syncytia).

To carry out this test, it is necessary to transfect the said 10 expression vectors, containing the mutated envelopes, into feline fibroblasts CrFK, in accordance with the following procedure:

A feline fibroblast cell line CrFK-H06T1/2 (OSBORNE et al., J. Gen. Virol., 1994, 75, 3641–3645) is cultured in a Dulbecco's modified Eagle medium supplemented with 10% calf serum.

The plasmids are purified using the Promega maxiprep system and are then extracted with phenol-chloroform. The transfection is carried out using the calcium phosphate precipitation method.

The transfection conditions are optimized and standardized using plasmids expressing the β-galactosi-dase or luciferase reporter genes.

To test the reactivity of the mutated domains with the sera of cats infected with FIV, an ELISA with the peptides according to the invention is carried out. The microtitre plates, containing 96 wells (Immunolon® 2), are coated with the said peptides, in a 0.1 M carbonate buffer pH 9.6 (5 µg/ml), at 4° C. overnight.

After blocking with 3% bovine serum albumin, feline sera diluted in PBS, 1% bovine serum albumin and 0.1% Tween 20 are added and incubated for 2 hours.

After 5 washes with PBS, 1% Tween 20, anti-cat antibodies conjugated with peroxidase are incubated for 1 hour. After 5 washes, the reaction is developed using ABTS at 0.4 mg/ml and by reading the optical density 30 min later.

In the same manner, the reactivity of the mutated domains can be tested with human sera infected with HIV-1. In this case, the procedure is the same, except for the use of 5% foetal calf serum in place of the bovine serum albumin.

Results:

Formation of syncytia:

The mutated vectors containing the sequences ID No. 1 to No. 10, produce syncytia, as illustrated in Table I below:

TABLE I

| Peptides | | No. syncytia (No. nuclei) (0.5 μg) | No. syncytia (No. nuclei) (2 μg) | ELISA >25% TM2 experiment | ELISA >25% TM2 natural |
|---|---|---|---|---|---|
| TM2 | CNQNQFFCK | 991 (5–100) | 1900 (15–150) | | |
| f8 | CNQNQWLCK | 522 (5–100) | 1280 (5–100) | 1/8 | 1/11 |
| fd | CNQNQFLCK | ND°° | 500 (5–90) | 5/8 | 9/11 |
| fh | CNQNQLWCK | 200 (5–70) | 415 (5–70) | 4/8 | 3/11 |
| fm | CNQNQPFCK | 108 (5–50) | 170 (5–50) | 1/8 | 2/11 |
| n14 | CEHQHFFCK | 187 (5–20) | 754 (5–50) | 0/8 | 2/11 |
| n19 | CSMGTFFCK | 156 (5–30) | 408 (5–80) | 0/8 | 1/11 |
| n67 | CLTDSFFCK | +* | 800 (5–70) | 0/8 | 0/11 |
| n73 | CELKNFFCK | 160 (5–20) | 700 (5–40) | 0/8 | 1/11 |
| n92 | CRPAAFFCK | 114 (5–30) | 200 (5–30) | NI# | NI# |
| 0 | | 3 (5–7) | 4 (5–7) | | |

*>> 100 syncytia/well
°°ND: not determined
NI: not interpretable in the ELISA-peptide, because of the background noise in the reaction of the peptide n92 with control sera of noninfected cats.

The existence of cross-reactivity of the peptide n92 with the peptide TM2 was however ruled out by competition experiments between the two peptides.

The mutated vector pM5Δ20, containing a mutated fragment of the HIV PID was tested in another experiment and also showed the formation of syncytia.

FIG. 3 illustrates the results obtained with the MS vector (compared with the wild-type W).

The chimeras HIV/FIV M5 are capable of inducing the formation of syncytia (FIG. 3) which are smaller in size (5–20 nuclei, 48 hours after transfection) than those induced by the wild-type (W).

The size and the number of syncytia induced by MS increases with time up to 72 hours.

Immunological reactivity:

The modifications produced in the immunological properties of the PIDs by the mutations which preserve the fusogenic capacity of the mutant envelopes are tested by "peptide ELISA".

The peptides corresponding to the mutated PID (Table I) are synthesized and used to coat ELISA micro-plates. 8 sera of cats, experimentally infected with 4 different isolates of FIV and 11 sera obtained from naturally infected cats are tested in order to evaluate the reactivity of these peptides.

The optical density values obtained with the mutant PID peptides are compared with the values obtained with the wild-type PID peptide (TM2) comprising the peptide P237.

A substantial reduction in the reactivity of most of the mutants is highlighted relative to the TM2 peptide.

Table I above shows, for each peptide, the number of sera which showed a reactivity of more than 25% compared with the reactivity of the TM2 peptide.

In some cases, with the sera which showed a reactivity with the mutant peptides, competition assays were carried out between the TM2 peptide and the mutated peptides.

In no case does a mutated peptide inhibit the reactivity of the serum towards the TM2 peptide, whereas the TM2 peptide completely inhibits the reactivity of the sera of cats infected with the mutated proteins.

These results show that the mutations introduced into the FIV PID greatly modify its recognition by sera of cats infected with an FIV (significantly modified immunoreactivity).

Cross-reactivity between the PIDs of FIV and HIV-1:

Two ELISAs were developed to test either the reactivity of the FIV PID with human serum infected with HIV-1, or the reactivity of the HIV-1 PID with cat serum infected with FIV.

The reactivity of the sera of 8 patients infected with HIV-1 and of 10 cats naturally infected with FIV, with the peptides corresponding to the PIDs either of HIV-1 or FIV, was tested with an ELISA.

The peptides p237 and SP89029 (ANRS Catalogue, 1994) corresponding to the FIV and HIV-1 sequences (PID) respectively and 2 peptides chemically cyclized between the two cysteines (Y-15-Vc (YQELGCN NOFFCLV) and L-15-Tc (LLGIWGCSGKLICTT) respectively for FIV and HIV-1), so as to mimic the natural folding, were used to coat the microtitre plates.

The sera of individuals infected with HIV-1 react strongly with the peptides containing a PID derived from HIV-1 (SP89029 and L-15-Tc), but not with the FIV peptides, that is to say the peptides containing a PID derived from FIV (P237 and Y-15-Vc) and, correspondingly, the sera of cats infected with FIV recognize the FIV peptides, but not the HIV-1 peptides.

Thus, no cross-reaction can be detected between the two PIDs. This allows the use of an appropriate peptide ELISA to monitor the anti-HIV-1 vaccination procedures based on chimeric envelopes containing the FIV PID sequence in the HIV-1 context or other mutations which modify the antigenic properties of the HIV-1 PID.

A similar approach is also possible in the case of vaccination against FIV, using an HIV-1 PID or other mutated sequences of the FIV envelope.

EXAMPLE 3

Gene Vaccination

The administration of the FIV env gene products as defined above, by injection of crude DNA, was studied so as to allow a vaccinal procedure which would allow analysis of the immune response of the wild-type envelope proteins, compared with the envelopes mutated in the PID region.

The expression vector Env pTΔ20, derived from the infectious molecular clone of FIV p34TF10, by deletion of the gag and pol genes, is used to vaccinate cats.

The vector pTΔ20 is injected intramuscularly into 4 cats (4 injections of 200–400 µg of DNA). The antibody response is analysed using 4 different peptides corresponding to the linear B cell epitopes (SU2, SU3, TM2 and TM4) by ELISA and by immunoprecipitation of the Env glycoproteins, from lysates of a cell line FL4, infected with FIV, after $^{35}$S labelling.

3 of the 4 cats show a weak response to at least 2 peptides. One serum is also capable of precipitating the envelope glycoproteins (last dilution tested 1:320) from the FL4 cells. These results indicate that the immunization based on the env gene indeed leads to an immune response and therefore to its use in vaccines with the mutated Env proteins.

EXAMPLE 4

Construction of Mutants in the HIV-1 Context (Chimeras in which a PID of FIV or SIV Replaces the Wild-Type PID of HIV-1, in an HIV-1 Env Sequence): Functionality and Reactivity of the Products Obtained The sequence encoding the HIV-1 Env protein is modified so that the sequences encoding the peptide fragments SEQ ID No. 11 or 12, as defined above, are inserted in place of the sequence encoding the peptide fragment contained between the two cysteines of the HIV-1 PID.

Sequences encoding modified Env proteins are thus obtained in which the sequence contained between the two cysteines of the HIV-1 PID, in the HIV-1 LAI envelope, has been replaced by the corresponding sequences of the feline immunodeficiency virus (FIV) or of SIV.

To do this, the SmaI-BamHI fragment of the HIV-1 LAI envelope was subcloned into the plasmid pTZ18 and the mutations were introduced by site-directed mutagenesis (Kunkel), using oligonucleotides corresponding to the mutations, as specified above:

P s t F I V ;

5'-ATTTGGGGTTGCAATCAAAATCAATTCTTCTGCACCACTGCAGTGCCTTGGAAT-3';

P s t S I V ;

5'-ATTTGGGGTTGCGCGTTTAGACAAGTCTGCACCACTGCAGTGCCTTGGAA-3',

To allow screening of the recombinant clones, a Pst1 restriction site was also introduced into the envelope upstream of the PID, so as not to modify the amino acid sequence. The mutated fragment was then cloned into the expression vector pMA243 (DRAGIC T. et al., J. Virol., 1992, 66, 4794–4802), in order to analyse the properties of the mutant envelopes.

The capacity of the mutant envelopes to induce fusion between cell membranes, a property of the wild-type envelope, was analysed using a fusion test carried out after transfection of the envelopes into COS cells and coculture with HeLa cells expressing the HIV-1 cellular receptor CD4 and the β-galactosidase gene placed under the control of the HIV-1 LTR (DRAGIC T. et al., cited above; CHARNEAU P. et al., J. Virol., 1992, 66, 2814–2820). The fusion of two cell types, mediated by the HIV-1 envelope, activates the expression of β-galactosidase and the fused cells can be detected by a blue colour, derived from an enzymatic reaction. After transfection of 3 µg of DNA/well into 6-well plates, the two mutant envelopes are induced by cellular fusions and the formation of syncytia (Table II). In particular, the chimeric clone containing the FIV sequence in the context of the HIV-1 envelope showed good efficiency in inducing cell fusion.

TABLE II

| Clone | No. of blue foci/well* |
|---|---|
| WT (wild-type HIV-1 LAI) | 3500 |
| HIV-1/FIV | 1400 |
| HIV-1/SIV | 200 |

*mean of the count for 3 wells

The expression and maturation of the mutant envelopes were analysed by metabolic labelling with [$^{35}$S] methionine and cysteine of the transfected cells, followed by immunoprecipitation of the envelope proteins with a pool of human sera obtained from seropositive donors. This study showed that the envelope precursors of the two mutants were produced in a quantity comparable to the wild-type clone. The precursors of the two mutant envelopes were correctly cleaved to give rise to two subunits of the mature complex of the envelope, the extracellular glycoprotein (SU) and the transmembrane glycoprotein (TM). The immunoprecipitation of the SU glycoproteins of the culture supernatants showed that the SUs of the mutated envelopes were liberated into the supernatant in a quantity greater than that of the wild-type envelope.

As evident from the above, the invention is not at all limited to its embodiments, implementations and applications which have just been described more explicitly; it embraces on the contrary all the variants thereof which may occur to a specialist in this field, without departing from the scope or from the framework of the present invention.

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Cys Asn Gln Asn Gln Trp Leu Cys Lys
1               5

(2) INFORMATION FOR SEQ ID NO:2:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Cys Asn Gln Asn Gln Phe Leu Cys Lys
1               5

(2) INFORMATION FOR SEQ ID NO:3:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:3:

Cys Asn Gln Asn Gln Leu Trp Cys Lys
1               5

(2) INFORMATION FOR SEQ ID NO:4:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Cys Asn Gln Asn Gln Pro Phe Cys Lys
1               5

(2) INFORMATION FOR SEQ ID NO:5:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:5:

Cys Glu His Gln His Phe Phe Cys Lys
1               5

(2) INFORMATION FOR SEQ ID NO:6:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:6:

Cys Ser Met Gly Thr Phe Phe Cys Lys
1               5

(2) INFORMATION FOR SEQ ID NO:7:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:7:

Cys Leu Thr Asp Ser Phe Phe Cys Lys
1               5

(2) INFORMATION FOR SEQ ID NO:8:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:8:

Cys Glu Leu Lys Asn Phe Phe Cys Lys
1               5

(2) INFORMATION FOR SEQ ID NO:9:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:9:

Cys Arg Pro Ala Ala Phe Phe Cys Lys
1               5

(2) INFORMATION FOR SEQ ID NO:10:

(i) SEQUENCE CHARACTERISTICS:
             (A) LENGTH: 13 amino acids
             (B) TYPE: amino acid
             (C) STRANDEDNESS: single
             (D) TOPOLOGY: linear -continued

```
        (ii) MOLECULE TYPE: peptide (xi) SEQUENCE DESCRIPTION: SEQ ID NO:10:

Glu Leu Gly Cys Ser Gly Lys Leu Ile Cys Lys Ile Pro
1               5                  10

(2) INFORMATION FOR SEQ ID NO:11:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Ile Trp Gly Cys Asn Gln Asn Gln Phe Phe Cys Thr Thr Ala Val Pro
1               5                  10                  15

Trp Asn (2) INFORMATION FOR SEQ ID NO:12:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Ile Trp Gly Cys Ala Phe Arg Gln Val Cys Thr Thr Ala Val Pro Trp
1               5                  10                  15

(2) INFORMATION FOR SEQ ID NO:13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE"

(xi) SEQUENCE DESCRIPTION: SEQ ID NO:13:

TGTAATCAAA ATCAATGGCT TTGCAAA                                    27

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE"

(xi) SEQUENCE DESCRIPTION: SEQ ID NO:14:

TGTAATCAAA ATCAATTTTT ATGCAAA                                    27

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
```

(D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:15:

TGTAATCAAA ATCAATTGTG GTGCAAA                                              27

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:16:

TGTAATCAAA ATCAACCTTT TTGCAAA                                              27

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:17:

TGTGAACATC AGCATTTTTT CTGCAAA                                              27

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:18:

TGTAGTATGG GGACGTTTTT CTGCAAA                                              27

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO:19:

TGTTTGACAG ATTCGTTTTT CTGCAAA                                              27

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear -continued

```
    (ii) MOLECULE TYPE: other nucleic acid
        (A) DESCRIPTION: /desc = "OLIGONUCLEOTIDE"

(xi) SEQUENCE DESCRIPTION: SEQ ID NO:20:

TGTGAACTCA AAAACTTTTT CTGCAAA                                    27

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:21:

TGTCGGCCAG CTGCTTTTTT CTGCAAA                                    27

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:22:

GAGCTCGGAT GTTCTGGAAA ACTCATTTGC AAAATCCCT                       39

(2) INFORMATION FOR SEQ ID NO:23:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:23:

ATTTGGGGTT GCAATCAAAA TCAATTCTTC TGCACCACTG CAGTGCCTTG GAAT       54

(2) INFORMATION FOR SEQ ID NO:24:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:24:

ATTTGGGGTT GCGCGTTTAG ACAAGTCTGC ACCACTGCAG TGCCTTGGAA            50
```

We claim:

1. A purified mutant lentivirus Env protein comprising a polypeptide having at least one mutated amino acid sequence of a transmembrane protein of a principal immunodominant domain (PID), wherein said amino acid sequence is mutated between two cysteines.

2. The purified mutant lentivirus Env protein according to claim 1, wherein said lentivirus is selected from the group consisting of the feline immunodeficiency virus (FIV), the human immunodeficiency virus (HIV), and the caprine arthritis and encephalitis virus (CAEV).

3. An isolated polynucleotide comprising a nucleotide sequence encoding the mutant Env protein according to claim 1.

4. The polynucleotide according to claim 3 containing a sequence selected from the group consisting of SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, and SEQ ID No. 24.

5. The isolated polynucleotide according to claim 3, wherein said nucleotide sequence encodes a mutant FIV Env protein.

6. The isolated polynucleotide according to claim 3, wherein said nucleotide sequence encodes a mutant HIV Env protein.

7. The isolated polynucleotide according to claim 3, wherein said nucleotide sequence encodes a mutant CAEV Env protein.

8. An expression vector comprising the polynucleotide of claim 3.

9. The expression vector according to claim 8, wherein said polynucleotide encodes a modified PID.

10. The expression vector according to claim 9, wherein said encoded modified PID is selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, and SEQ ID No. 12.

11. A process of producing an antibody comprising the steps of:

(a) administering the polypeptide of claim 1 to a host to induce formation of said antibody; and (b) isolating the antibody from the host.

12. An immunogenic composition comprising at least one expression vector according to claim 8.

13. An immunogenic composition comprising at least one expression vector according to claim 9.

14. An immunogenic composition comprising at least one expression vector according to claim 10.

15. An immunogenic composition comprising at least one mutated Env protein according to claim 1.

16. A lentivirus-specific diagnostic reagent, comprising a polypeptide sequence according to claim 2.

* * * * *